US00PP27791P2

(12) United States Plant Patent
Bacon

(10) Patent No.: US PP27,791 P2
(45) Date of Patent: Mar. 21, 2017

(54) GRAPEVINE PLANT NAMED 'SUGRAFORTYEIGHT'

(50) Latin Name: *Vitis vinifera*
Varietal Denomination: Sugrafortyeight

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 14/757,378

(22) Filed: Dec. 22, 2015

(51) Int. Cl.
*A01H 5/08* (2006.01)

(52) U.S. Cl.
USPC ..... Plt./205

(58) Field of Classification Search
USPC ..... Plt./205
See application file for complete search history.

*Primary Examiner* — Annette Para
(74) *Attorney, Agent, or Firm* — Knobbe, Martens, Olson & Bear, LLP

(57) ABSTRACT

A new and distinct grapevine variety 'Sugrafortyeight' is characterized by a midseason harvest date, the production of a large-sized, black, broad elliptic berry and a very large bunch size. The berries of 'Sugrafortyeight' are very firm and begin to ripen earlier than 'Sugrathirtyfour' (U.S. Plant Pat. No. 19,750) or 'Autumn Royal' (unpatented). The new variety 'Sugrafortyeight' is characterized by a broad elliptic berry shape compared to the elongated berry shape of both 'Autumn Royal' (unpatented) and 'Sugrathirteen' (U.S. Plant Pat. No. 10,434).

1 Drawing Sheet

Latin name of the genus and species claimed: *Vitis vinifera.*

Variety denomination: 'SUGRAFORTYEIGHT'.

BACKGROUND AND SUMMARY OF THE INVENTION

This application relates to the discovery and asexual propagation of a new and distinct variety of grapevine, 'Sugrafortyeight', as herein described and illustrated. The new variety was first selected as breeder number 'GR384B' by Terry A. Bacon in Wasco, Kern County, Calif. in August 2013. The variety was originated by controlled hybridization.

The new variety 'Sugrafortyeight' is characterized by a midseason harvest date, the production of a large-sized, black, broad elliptic berry and a very large bunch size. The berries of 'Sugrafortyeight' are very firm.

The seed parent is the varietal selection 'Sugrathirtyfive' (U.S. Plant Pat. No. 20,491) and the pollen parent is the varietal selection 'Sugrathirtyfour' (U.S. Plant Pat. No. 19,750). The parent varieties were first crossed in May 2011. The date of first sowing was March 2012, and the date of first flowering was May 2013.

The new variety 'Sugrafortyeight' was first asexually propagated in December 2013 in Wasco, Kern County, Calif., by Terry A. Bacon using hardwood cuttings.

The new variety 'Sugrafortyeight' differs from its seed parent 'Sugrathirtyfive' (U.S. Plant Pat. No. 20,491) in that the new variety 'Sugrafortyeight' begins ripening about August 5$^{th}$ compared to about September 1$^{st}$ for 'Sugrathirtyfive'. The new variety 'Sugrafortyeight' also differs from its seed parent 'Sugrathirtyfive' in that the new variety 'Sugrafortyeight' has a black berry while 'Sugrathirtyfive' has a green berry.

The new variety 'Sugrafortyeight' is similar to its pollen parent 'Sugrathirtyfour' (U.S. Plant Pat. No. 19,750) in appearance. However, the new variety 'Sugrafortyeight' begins ripening about August 5$^{th}$ compared to September 25$^{th}$ for 'Sugrathirtyfour'.

The new variety has a berry color similar to that of 'Autumn Royal' (unpatented) and 'Sugrathirteen' (U.S. Plant Pat. No. 10,434). However, the beginning of ripening is August 5$^{th}$ for the new variety, compared to August 25th for 'Autumn Royal' and July 20th for 'Sugrathirteen'. The new variety also has a broad, elliptic berry shape compared to an elongated berry shape for both 'Autumn Royal' and 'Sugrathirteen' (U.S. Plant Pat. No. 10,434).

The new 'Sugrafortyeight' variety has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration shows typical specimens of the foliage and fruit of the present new grape variety 'Sugrafortyeight'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to 'Sugrafortyeight' plants grown in the vicinity of Wasco, Kern County, Calif. during 2015, and is believed to apply to plants of the variety grown under similar conditions of soil and climate elsewhere.

VINE

General: (measurements taken on a three year old plant).

- *Vine size*.—Medium. Height: Approximately 2.0 m. Width: Approximately 2.5 m.
- *Vigor*.—Vigorous.
- *Density of foliage*.—Dense.
- *Productivity*.—Very productive.
- *Crop load*.—Approximately 34 kg per vine after thinning.
- *Own root*.—Yes.
- *Training method*.—Typically spur pruned leaving 2 bud spurs.
- *Resistance*.—Neither resistance nor susceptibility to diseases or pests has been observed in this variety.

Trunk:

- *Shape*.—Stocky to medium.
- *Diameter*.—Approximately 7.5 mm (at 30 cm above the soil line).
- *Straps*.—Short.
- *Surface texture*.—Medium shaggy.
- *Inner and outer bark color*.—Inner bark mainly Dark Greyed-Orange 177A and Medium Greyed-Orange 173C with highlights of about Medium Greyed-White 156C in outer bark.

SHOOTS

Young shoot:

- *Form of tip*.—Wide open.
- *Intensity of anthocyanin coloration of tip*.—Absent or very weak.
- *Density of prostrate hairs on tip*.—Sparse.
- *Density of erect hairs on tip*.—Absent or very sparse.
- *Color*.—About Medium Yellow-Green 144B.

Woody shoot (observations made in the middle third of shoot):

- *Attitude before tying*.—Semi-drooping to drooping.
- *Growth of axillary shoots*.—Medium strong, mainly 17 to 30 cm.
- *Internode length*.—Long, Approximately 12 cm to 14 cm.
- *Width at node*.—Approximately 13 mm.
- *Cross section*.—Circular.
- *Surface texture*.—Striated.
- *Main color*.—About Medium Greyed-Orange 166C.
- *Color of dorsal side of internode*.—Mainly about Medium Greyed-Orange 166C.
- *Color of ventral side of internode*.—Mainly about Medium Greyed-Orange 166D.
- *Color of dorsal side of node*.—About Medium Yellow-Green 146C with Medium Greyed-Orange 166D.
- *Color of ventral side of node*.—About Medium Yellow-Green 146C with Medium Greyed-Orange 166D.
- *Density of erect hairs on nodes*.—Absent or Very Sparse.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—About 4 cm.
- *Color*.—About Light Yellow-Green 148D in mid-summer.
- *Form*.—Bifurcated.
- *Number of consecutive tendrils*.—Up to 2.
- *Length of tendril*.—Medium, approximately 16.5 cm.

LEAVES

Young leaves:

- *Color of upper surface of first 4 distal unfolded leaves*.—About Medium Green 138B.
- *Average intensity of anthocyanin coloration of six distal leaves prior to flowering*.—Absent.
- *Density of prostrate hairs between veins at lower surface of 4th distal unfolded leaf*.—Absent or very sparse.
- *Density of erect hairs between veins at lower surface of 4th distal unfolded leaf*.—Absent or very sparse.
- *Density of prostrate hairs on veins at lower surface of 4th distal unfolded leaf*.—Absent or very sparse.
- *Density of erect hairs on veins at lower surface of 4th distal unfolded leaf*.—Absent or very sparse.

Mature leaves (observations made in the middle third of shoot):

- *Average length*.—Large, approximately 9 cm.
- *Average width*.—Large, approximately 14 cm.
- *Shape of blade*.—Pentagonal.
- *Number of lobes*.—Approximately 5.
- *Mature leaf profile*.—Undulate.
- *Blistering surface of blade upper surface*.—Absent or very weak.
- *Leaf blade tip*.—In the plane of the leaf.
- *Undulation of margin*.—Slight.
- *Thickness*.—Average — typical of *Vitis vinifera* species.
- *Overall shape of teeth*.—Mixture of both sides straight and both sides convex.
- *Length of teeth*.—Medium, ranging from about 5 mm to 10 mm.
- *Ratio length/width of teeth*.—Very small.
- *General shape of petiole sinus lobes*.—Half open.

*Tooth at petiole sinus*.—Absent.
*Petiole sinus limited by veins*.—Absent.
*Shape of upper lateral sinus lobes*.—Slightly to strongly overlapping.
*Depth of upper lateral sinuses*.—Medium, approximately 20 mm to 40 mm.
*Density of prostrate hairs between veins on lower surface of blade*.—Absent to very sparse.
*Density of erect hairs between veins on lower surface of blade*.—Absent to very sparse.
*Density of prostrate hairs on main veins on lower surface of blade*.—Absent to very sparse.
*Density of erect hairs on main veins on lower surface of blade*.—Absent to very sparse.
*Density of prostrate hairs on main veins on upper surface of blade*.—Absent to very sparse.
*Autumn coloration of leaves*.—Mainly Dark Green 138A but some leaves mixed Dark Green 138A with Dark Greyed-Purple 187A and Dark Yellow-Green 154A.

Upper leaf surface:
*Color*.—About Dark Green 139A.
*Surface texture*.—Smooth.
*Surface appearance*.—Dull.
*Anthocyanin coloration of main veins*.—Absent or very sparse.

Lower leaf surface:
*Color*.—About Medium Green 138B.
*Surface texture*.—Smooth.
*Surface appearance*.—Dull.
*Anthocyanin coloration of main veins*.—Absent or very sparse.

Petiole:
*Length of petiole*.—Medium, approximately 9 cm to 12 cm. Typically about 11 cm.
*Diameter*.—Approximately 4 mm.
*Length of petiole compared to middle vein*.—Nearly equal.
*Density of prostrate hairs on petiole*.—Absent.
*Density of erect hairs on petiole*.—Absent.
*Color*.—About Medium Green 138B becoming Light Greyed-Red 182D as it ages.

Buds:
*Shape*.—Conical.
*Size*.—Medium, approximately 3 mm wide×4 mm long.
*Position*.—Slightly held out.
*Bud fruitfulness*.—Basal, mostly fruitful $3^{rd}$ to $5^{th}$ bud position.
*Time of bud burst*.—Medium for area of Wasco, Calif. Approximately March 16th.

FLOWERS

General:
*Flower type*.—Fully developed stamen and fully developed gynoecium.
*Position of first flowering node*.—Usually $4^{th}$ to $5^{th}$ node of current season growth.
*Number of inflorescences per shoot*.—Approximately 1 to 2 with an average of about 1.5.
*Time of full bloom*.—Medium for area of Wasco, Calif. Approximately April 30th.

FRUIT

General:
*Ripening period*.—Midseason, beginning about August 5th with mid-ripe about August 12th.
*Use*.—Fresh market.
*Storage quality*.—Excellent.

Cluster:
*Form*.—Conical, shouldered.
*Cluster size* (*peduncle excluded*).—Large, about 870 gm.
*Cluster length* (*peduncle excluded*).—Medium, approximately 21 cm.
*Cluster width*.—Approximately 15 cm.
*Cluster weight*.—Large, approximately 870 g.
*Cluster density*.—Medium, loose and full.
*Number of berries*.—Approximately 85.

Peduncle:
*Length*.—Medium, approximately 2.2 cm.
*Diameter*.—Approximately 6 mm.
*Lignification of peduncle*.—Weak.
*Color*.—Medium Yellow-Green 146C.

Berry:
*Size*.—Very large.
*Dimensions*.—Longitudinal axis: Approximately 34 mm. Horizontal axis: Approximately 28 mm.
*Berry weight*.—Approximate natural weight averages 11.8 gr.
*Uniformity of size*.—Uniform.
*Shape*.—Broad elliptic.
*Cross section*.—Circular.
*Skin color* (*without bloom*).—About Dark Greyed-Purple 187A becoming Black 201A.
*Flesh color*.—Usually Medium Green 138B near the center and about Mediume Greyed-white 156D around the perimeter beneath the skin. Occasionally some Medium Red 41B developing around the perimeter as the berry matures.
*Anthocyanin color of flesh*.—Weak.
*Bloom* (*cuticular wax*).—Medium.
*Pedicel length*.—Approximately 7 mm.
*Pedicel thickness*.—Medium, approximately 1.8 mm.
*Berry separation from pedicel*.—Moderately easy.
*Seed traces*.—Berries contain 1 to 3 about Medium Greyed-White 156B, rudimentary soft seed traces per berry.
*Berry firmness*.—Very firm.
*Flesh juiciness*.—Juicy.
*Flesh texture*.—Crisp.
*Particular flavor*.—None.
*Refractometer test*.—About 19 Brix.
*Juice pH*.—About 3.6.
*Titratable acidity*.—About 0.49%.
*Brix:acid ratio*.—Approximately 38.8.

Skin:
*Thickness*.—Medium, about 175 μm.
*Texture*.—Smooth.
*Reticulation*.—Absent.
*Tenacity*.—Tenacious to flesh.
*Tendency to crack*.—Low.
*Sensitivity to sunburn*.—None or very low.

What is claimed is:

1. A new and distinct variety of grapevine as herein illustrated and described.

* * * * *

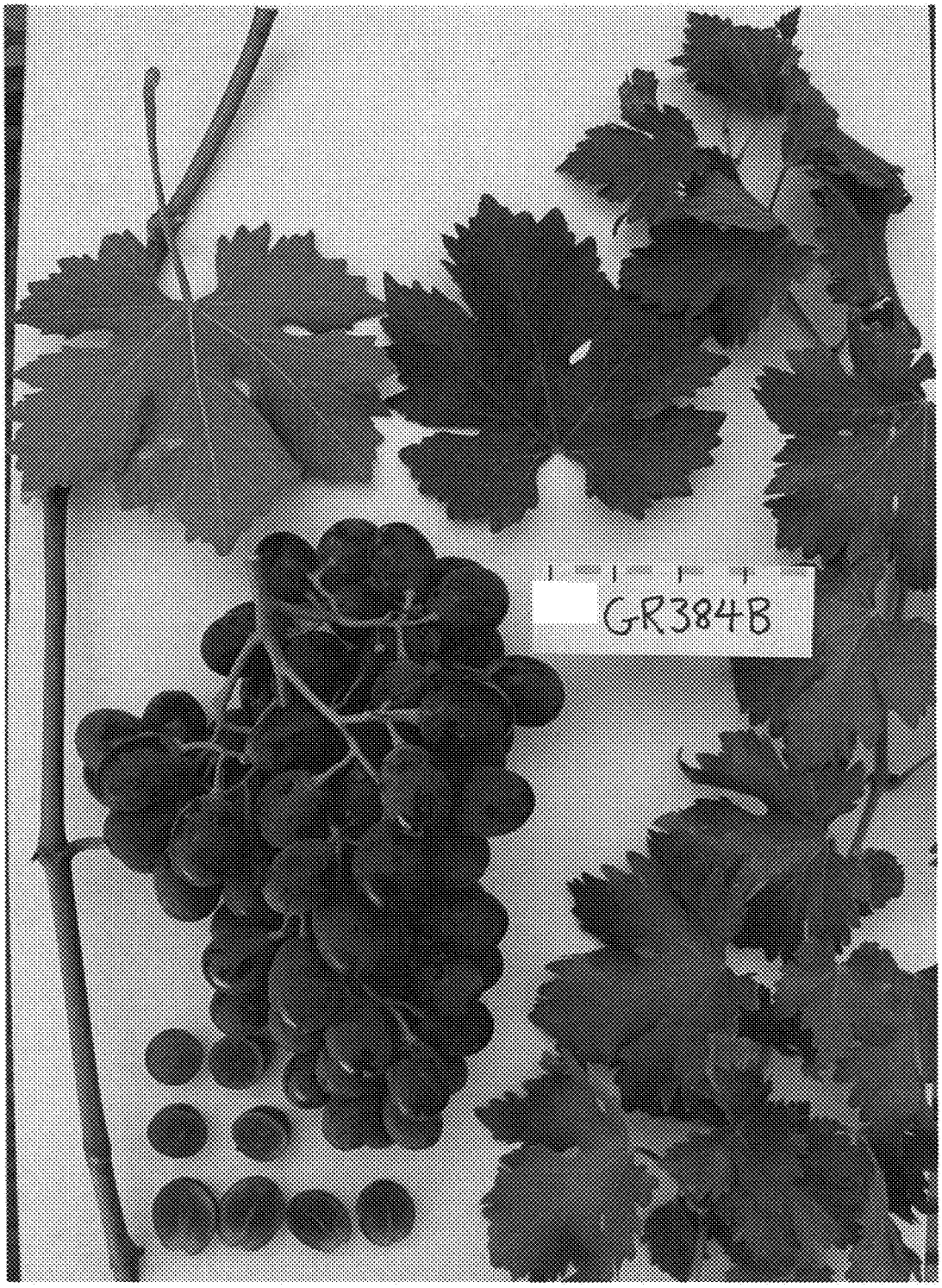
GR384B